(12) United States Patent
Takeuchi

(10) Patent No.: US 9,910,029 B2
(45) Date of Patent: Mar. 6, 2018

(54) BREATH DETECTION DEVICE, MOBILE TERMINAL AND TIME DISPLAY DEVICE

(71) Applicant: Seiko Epson Corporation, Tokyo (JP)

(72) Inventor: Junichi Takeuchi, Chino (JP)

(73) Assignee: SEIKO EPSON CORPORATION, Tokyo (JP)

( * ) Notice: Subject to any disclaimer, the term of this patent is extended or adjusted under 35 U.S.C. 154(b) by 0 days.

(21) Appl. No.: 14/729,347

(22) Filed: Jun. 3, 2015

(65) Prior Publication Data

US 2015/0355161 A1    Dec. 10, 2015

(30) Foreign Application Priority Data

Jun. 10, 2014    (JP) ................................. 2014-119956

(51) Int. Cl.
| | |
|---|---|
| *G01N 33/497* | (2006.01) |
| *G01N 19/10* | (2006.01) |
| *A61B 5/00* | (2006.01) |
| *A61B 5/087* | (2006.01) |
| *G01L 9/00* | (2006.01) |
| *G01L 9/02* | (2006.01) |
| *G01L 19/00* | (2006.01) |

(Continued)

(52) U.S. Cl.
CPC ........... *G01N 33/497* (2013.01); *A61B 5/087* (2013.01); *A61B 5/681* (2013.01); *G01L 9/0054* (2013.01); *G01L 9/025* (2013.01); *G01L 19/0092* (2013.01); *G01N 19/10* (2013.01); *A61B 5/0878* (2013.01); *A61F 4/00* (2013.01); *G01N 1/22* (2013.01); *G06F 3/011* (2013.01); *G06F 21/32* (2013.01); *H04M 2250/12* (2013.01); *H04W 88/02* (2013.01)

(58) Field of Classification Search
CPC . G01N 9/26; G01N 9/263; G01N 1/22; G01L 9/025; G01L 9/0054; G01L 19/0092; A61B 5/087
USPC ..................................................... 340/363.18
See application file for complete search history.

(56) References Cited

U.S. PATENT DOCUMENTS

| | | | | |
|---|---|---|---|---|
| 6,026,674 A | * | 2/2000 | Gammenthaler | .... B60K 28/063 180/272 |
| 2007/0189562 A1 | * | 8/2007 | Chiu | ................... F21V 23/0442 381/315 |

(Continued)

FOREIGN PATENT DOCUMENTS

| | | |
|---|---|---|
| JP | 08-234787 | 9/1996 |
| JP | 2002-148235 | 5/2002 |

(Continued)

*Primary Examiner* — Manish S Shah
*Assistant Examiner* — Timothy Graves
(74) *Attorney, Agent, or Firm* — Oliff PLC

(57) ABSTRACT

A breath detection device includes a breath-blowing unit in which breath is blown; a deflection amount sensor that detects pressure of the breath-blowing unit; a temperature sensor that detects a physical amount (temperature) different from the pressure of the breath-blowing unit; a storage unit that stores a determination reference which is a reference to determine whether or not breath is blown into the breath-blowing unit; and a determination unit that compares a detection result which is detected by the deflection amount sensor and the temperature sensor with the determination reference, and determines whether or not breath is blown into the breath-blowing unit.

10 Claims, 8 Drawing Sheets

(51) Int. Cl.
*G01N 1/22* (2006.01)
*A61F 4/00* (2006.01)
*G06F 3/01* (2006.01)
*H04W 88/02* (2009.01)
*G06F 21/32* (2013.01)

(56) References Cited

U.S. PATENT DOCUMENTS

2011/0000482 A1    1/2011  Gumaste et al.
2012/0304280 A1*  11/2012  Hayashida .......... G06F 21/6218
                                                    726/16
2014/0004908 A1*   1/2014  Park ...................... H04W 88/02
                                                    455/566
2014/0141761 A1*   5/2014  Yun .................... H04M 1/72569
                                                    455/418

FOREIGN PATENT DOCUMENTS

JP           2002-181763        6/2002
JP           2002-181767        6/2002
JP           2009-026124        2/2009
JP           2012-531974       12/2012
WO         20111003022  A1      1/2011
WO        WO 2013026902    *    2/2013   ............. A61B 5/097
WO        WO 2013026902 A1 *    2/2013   ............. A61B 5/087

* cited by examiner

BREATH DETECTION DEVICE, MOBILE TERMINAL AND TIME DISPLAY DEVICE

CROSS-REFERENCE TO RELATED APPLICATIONS

This application claims priority to Japanese Patent Application No. 2014-119956 filed on Jun. 10, 2014. The entire disclosure of Japanese Patent Application No. 2014-119956 is hereby incorporated herein by reference.

BACKGROUND

1. Technical Field

The present invention relates to a breath detection device, a mobile terminal, and a time display device.

2. Related Art

A device is known into which breath of a person is blown, and thereby ON/OFF of a switch is operated (for example, JP-A-8-234787).

A voice recognition device which is disclosed in JP-A-8-234787 includes a sensor which detects pressure of breath and a voice recognition unit. The voice recognition unit is configured to operate if breath is blown into the voice recognition device and the sensor detects pressure of the breath.

However, there is a problem in which, in a case in which the voice recognition device that is described in JP-A-8-234787 is used, for example, outside or the like, the sensor detects wind pressure and thereby the voice recognition unit unintentionally operates. In this case, there is a possibility that power consumption due to an unintentional operation of the voice recognition unit may increase, a malfunction caused by recognizing a peripheral voice or the like may occur.

SUMMARY

An advantage of some aspects of the invention is to provide a breath detection device, a mobile terminal, and a time display device which can accurately detect whether or not breath is blown.

The invention can be implemented as the following application examples.

Application Example 1

This application example is directed to a breath detection device including: a breath-blowing unit into which breath is blown; a pressure detection unit that detects pressure which is received by the breath-blowing unit, and outputs a signal; a physical amount detection unit that detects a physical amount different from the pressure and outputs a signal; a storage unit that stores a determination reference which is a reference to determine whether or not breath is blown into the breath-blowing unit; and a determination unit that compares the signal which is output from the pressure detection unit and the signal which is output from the physical amount detection unit with the determination reference, and determines whether or not breath is blown into the breath-blowing unit.

According to this application example, since the pressure of the breath-blowing unit and a physical amount other than the pressure are detected, the detection result is compared with the determination reference, and thereby determination is performed, it is possible to accurately detect whether or not breath is blown, compared to a case in which only a pressure is detected, the detected pressure is compared with the determination reference, and thereby determination is performed.

Application Example 2

In the breath detection device according to the application example, it is preferable that the physical amount detection unit includes a temperature sensor.

According to this application example, since detection results of pressure and temperature of the breath-blowing unit are compared with the determination reference and thereby determination is performed, it is possible to detect whether or not breath is blown. Thus, the breath detection device can be configured not to recognize that breath is blown as long as the detection results of each detection unit do not satisfy a predetermined condition of pressure and temperature based on the determination reference.

Application Example 3

In the breath detection device according to the application example, it is preferable that the pressure detection unit includes a pressure sensor, and the pressure sensor and the temperature sensor are integrally configured.

According to this application example, the pressure sensor and the temperature sensor can be configured as one element. Thus, it is possible to simplify a configuration of the breath detection device and to miniaturize the breath detection device, compared to a case in which the pressure sensor and the temperature sensor are separately provided.

Furthermore, since the pressure sensor and the temperature sensor are integrally configured, the pressure sensor and the temperature sensor can be disposed as closely as possible. As a result, temperature of the breath-blowing unit can be detected as accurately as possible.

Application Example 4

In the breath detection device according to the application example, it is preferable that the physical amount detection unit includes a humidity sensor.

According to this application example, since detection results of pressure and humidity of the breath-blowing unit are compared with the determination reference and thereby determination is performed, it is possible to detect whether or not breath is blown. Thus, the breath detection device can be configured not to recognize that breath is blown as long as the detection results of each detection unit do not satisfy a predetermined condition of pressure and humidity based on the determination reference.

Application Example 5

In the breath detection device according to the application example, it is preferable that the physical amount detection unit includes a microphone.

According to this application example, since detection results of pressure and a voice of the breath-blowing unit are compared with the determination reference and thereby determination is performed, it is possible to detect whether or not breath is blown. Thus, the breath detection device can be configured not to detect that breath is blown as long as the detection results of each detection unit do not satisfy a predetermined condition of pressure and a voice based on the determination reference.

Application Example 6

In the breath detection device according to the application example, it is preferable that the determination reference includes reference data that is a reference, and data of an audio that is detected by the microphone is compared with the reference data.

According to this application example, it is possible to more accurately determine whether or not breath is blown.

Application Example 7

In the breath detection device according to the application example, it is preferable that the determination reference is set based on information on breath that is blown in advance into the breath-blowing unit.

According to this application example, it is possible to more accurately determine whether or not breath is blown.

Application Example 8

This application example is directed to a mobile terminal including the breath detection device according to the application example described above.

According to this application example, it is possible to obtain a mobile terminal having a high reliability.

Application Example 9

This application example is directed to a time display device including the breath detection device according to the application example described above.

According to this application example, it is possible to obtain a time display device having a high reliability.

BRIEF DESCRIPTION OF THE DRAWINGS

The invention will be described with reference to the accompanying drawings, wherein like numbers reference like elements.

DESCRIPTION OF EXEMPLARY EMBODIMENTS

Hereinafter, a breath detection device, a mobile terminal, and a time display device according to the invention will be described in detail based on a preferred embodiment which is illustrated in the accompanying drawings.

To begin with, a mobile terminal which includes a breath detection device of the embodiment of the invention will be described.

First Embodiment

Figure 1:
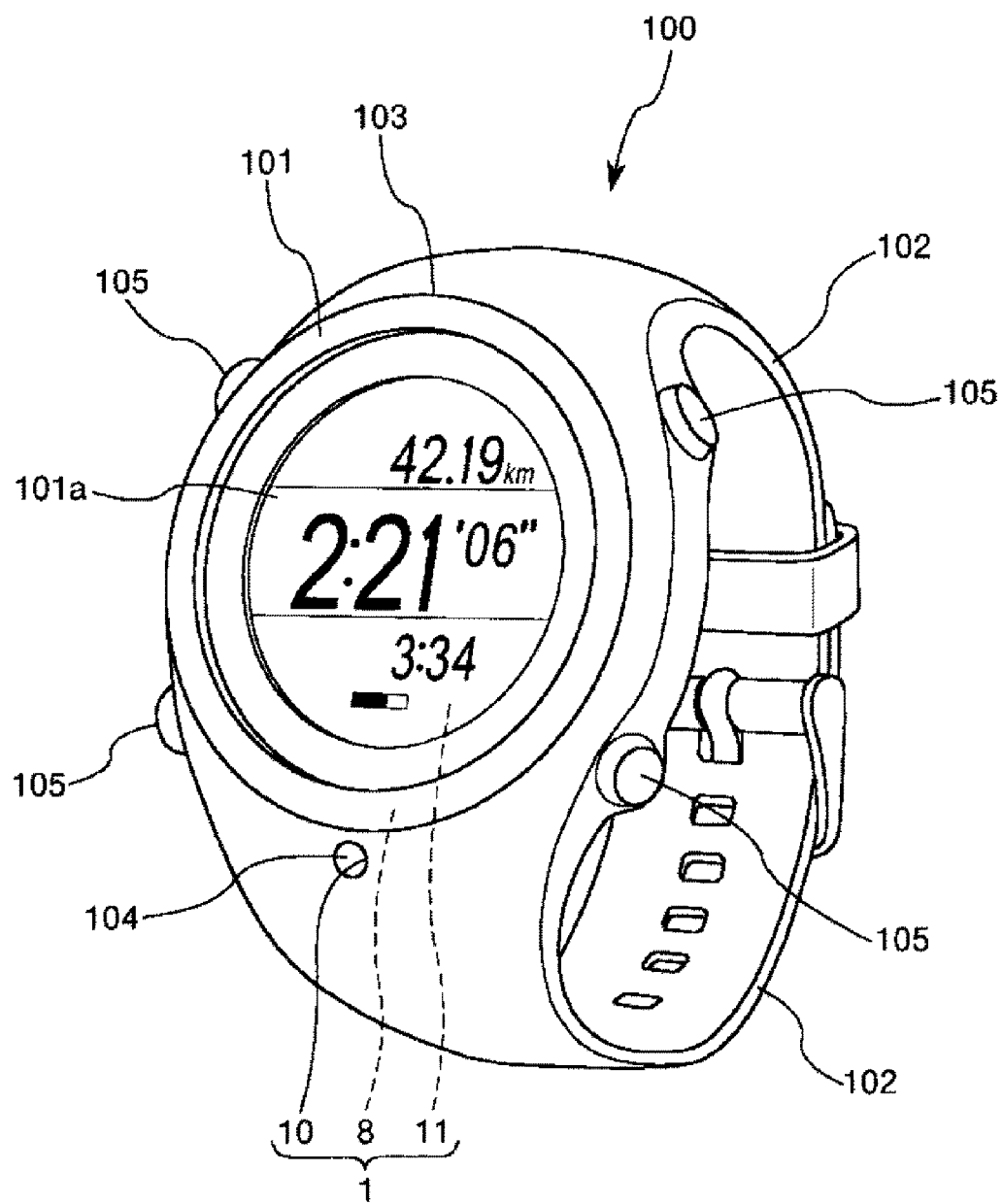
FIG. 1 is a perspective diagram of a mobile terminal that includes a first embodiment of a breath detection device according to the invention.
Figure 2:
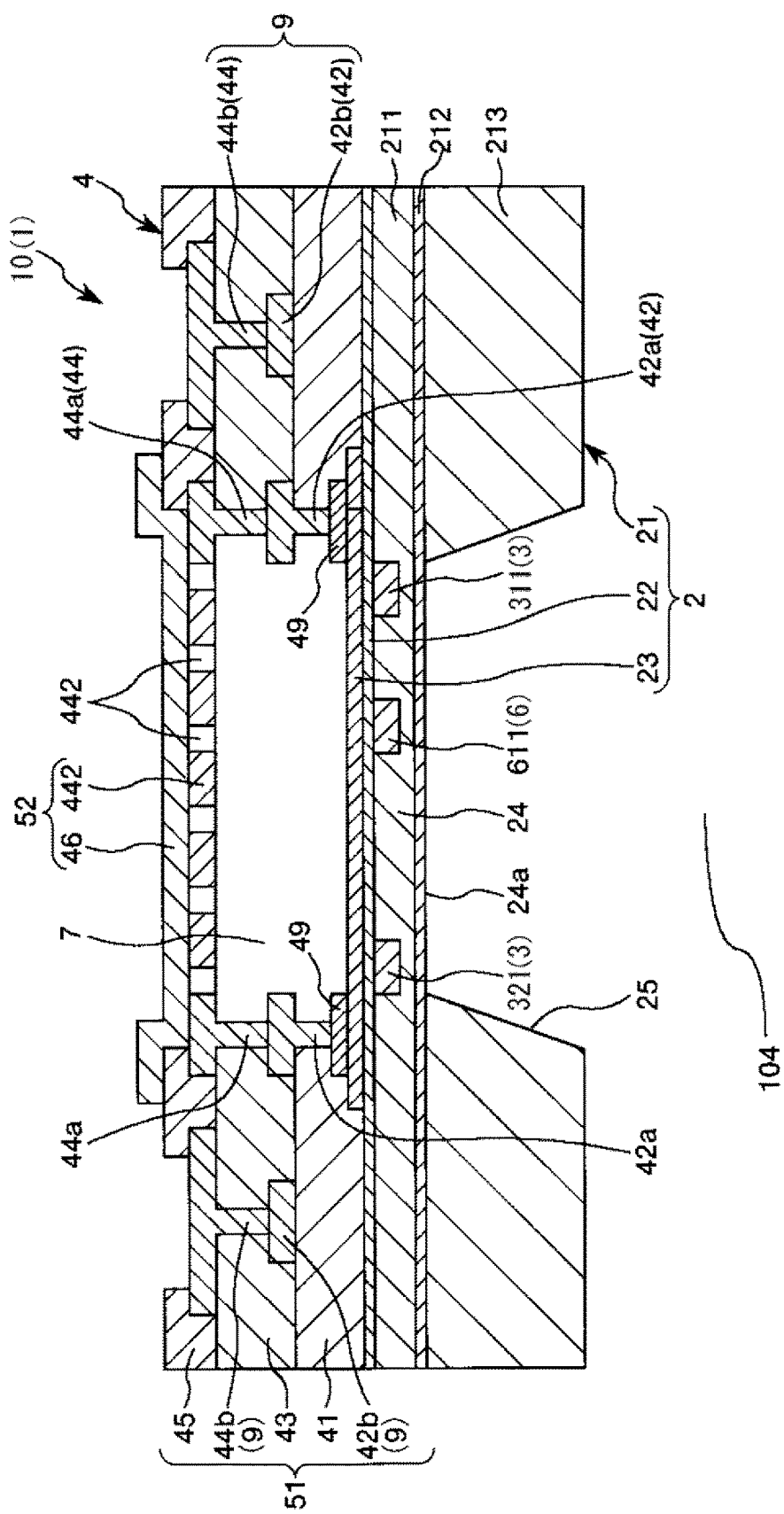
FIG. 2 is a sectional diagram illustrating a physical amount sensor that is illustrated in FIG. 1.
Figure 3:
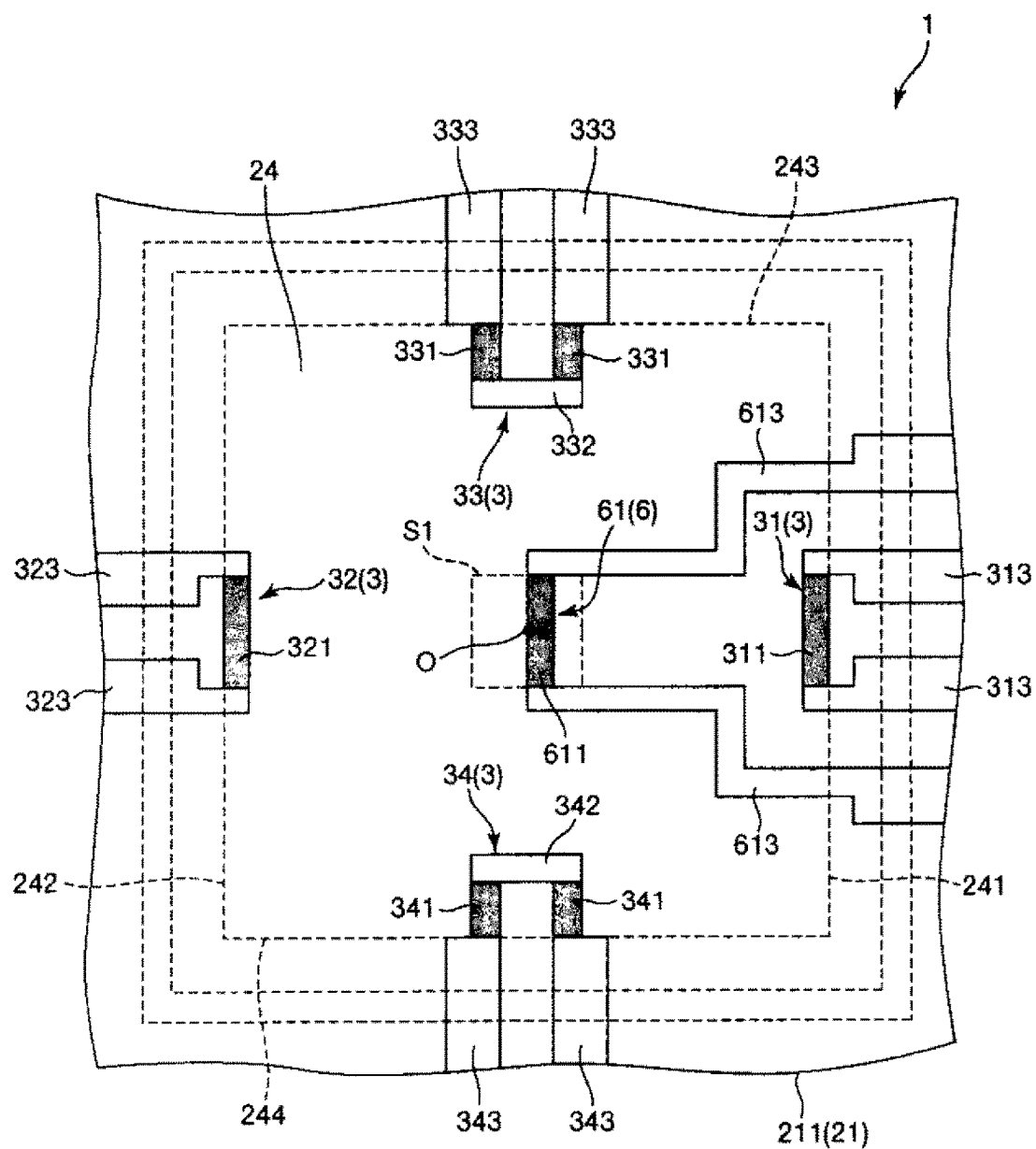
FIG. 3 is a plan diagram illustrating a deflection amount sensor and a temperature sensor that are included in the physical amount sensor which is illustrated in FIG. 1.
Figure 4:
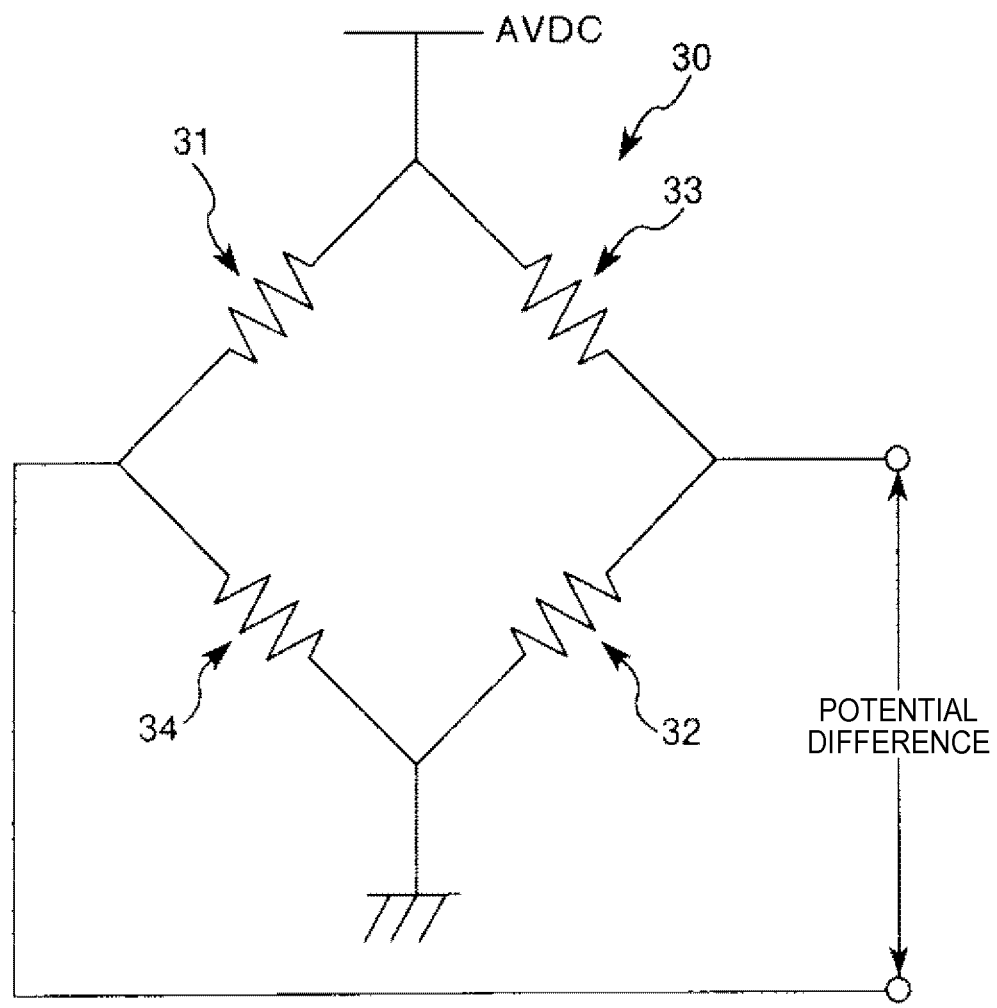
FIG. 4 is a diagram illustrating a circuit that includes the deflection amount sensor which is illustrated in FIG. 2.
Figure 5:
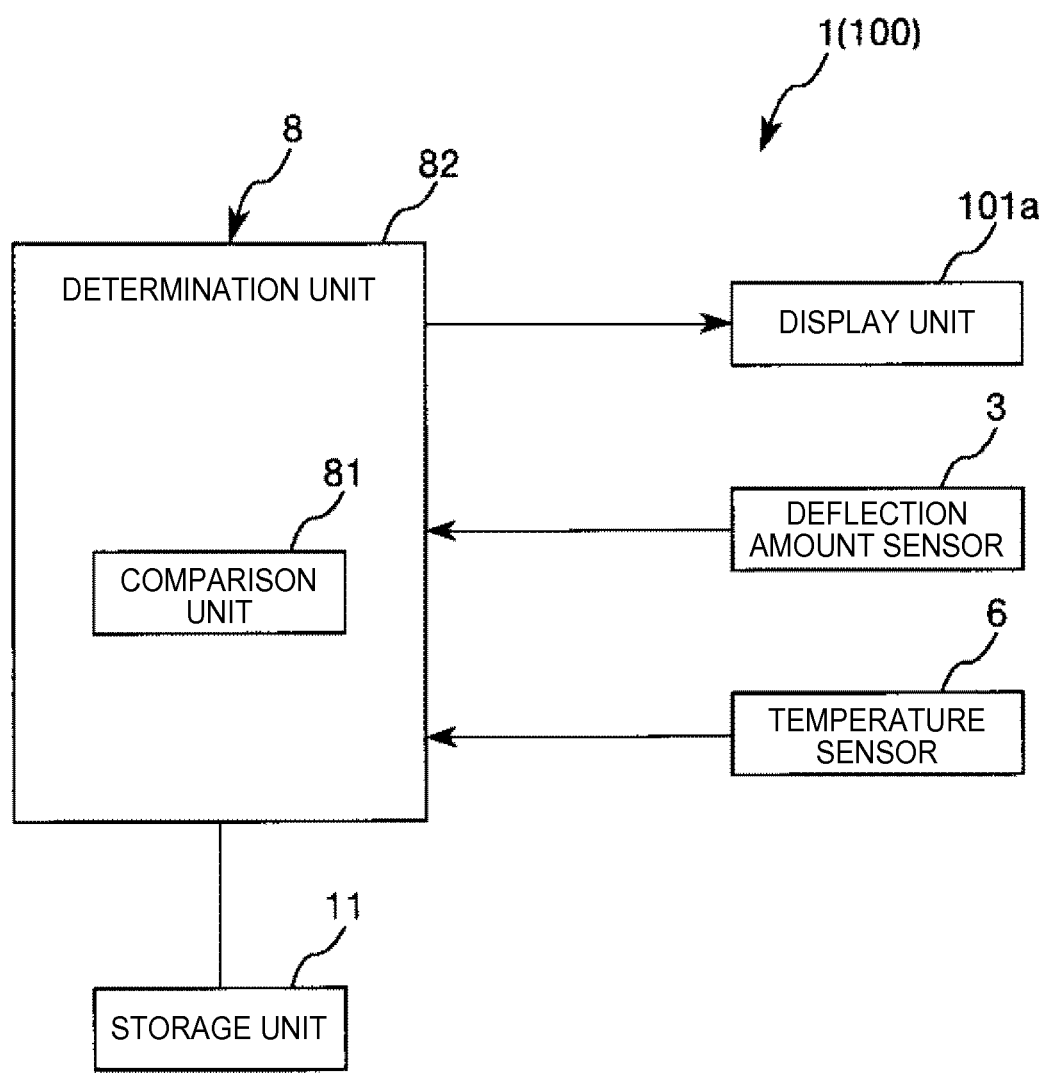
FIG. 5 is a block diagram illustrating a configuration of the breath detection device that is illustrated in FIG. 1.
Figure 6:
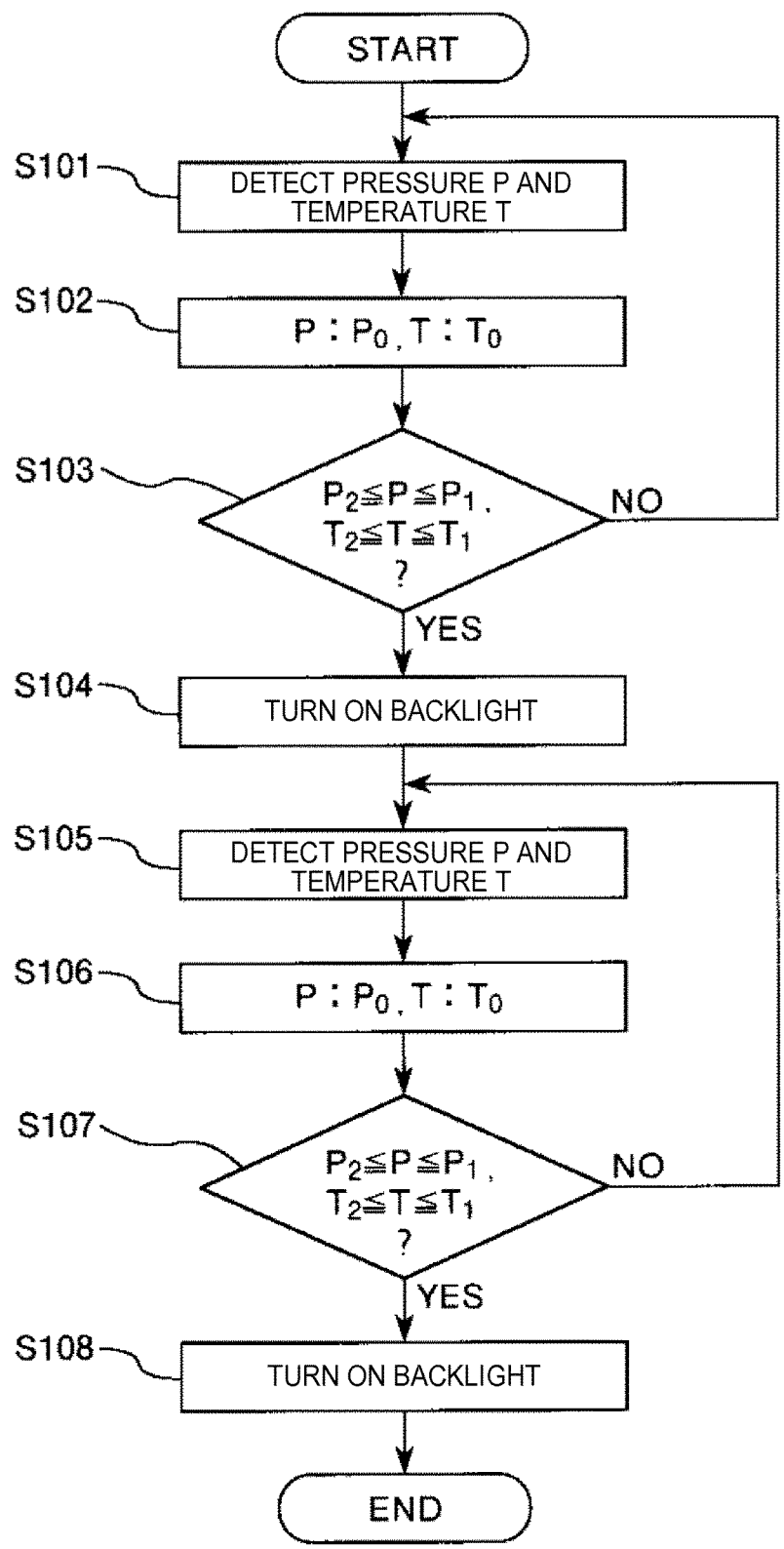
FIG. 6 is a flowchart illustrating a control of a control unit that is included in the breath detection device which is illustrated in FIG. 1.

FIG. 1 is a perspective diagram of a mobile terminal which includes a first embodiment of a breath detection device according to the invention. FIG. 2 is a sectional diagram illustrating a physical amount sensor that is illustrated in FIG. 1. FIG. 3 is a plan diagram illustrating a deflection amount sensor and a temperature sensor that are included in the physical amount sensor which is illustrated in FIG. 1. FIG. 4 is a diagram illustrating a circuit that includes the deflection amount sensor which is illustrated in FIG. 2. FIG. 5 is a block diagram illustrating a configuration of the breath detection device that is illustrated in FIG. 1. FIG. 6 is a flowchart illustrating a control of a control unit that is included in the breath detection device which is illustrated in FIG. 1.

As illustrated in FIG. 1, a mobile terminal 100 is a time display device of a wristwatch type. The mobile terminal 100 has a function in which various information sources are displayed, such as date, a height from the current position above sea level, weather, and a heart rate of a user, in addition to a current time, a stopwatch function, or the like.

The mobile terminal 100 includes a body section 101, and a pair of bands 102 which fixes the body section 101 to a wrist. In addition, each fixing band 102 is fixed by using a buckle which is provided on one side, and holes which are formed on the other side.

The body section 101 includes a case 103 which includes a display unit 101a which is configured by a liquid crystal display panel, and a breath detection device 1 of the embodiment of the invention which is embedded in the case 103. In addition, the breath detection device 1 includes a physical amount sensor 10, a control unit 8, and a storage unit 11. Hereinafter, the respective sections will be described.

As illustrated in FIG. 1, the case 103 is configured by a chassis, and contains the physical amount sensor 10, the control unit 8, the storage unit 11, a battery (not illustrated), and the like. In addition, in a side section of the case 103, a plurality of operation buttons 105 is provided. By operating the operation buttons 105, information which is displayed on the display unit 101a can be switched, or ON/OFF of a stopwatch or a backlight can be selected.

A breath-blowing hole (breath detection section) 104 is formed in the periphery of the display unit 101a of the case 103. The breath-blowing hole 104 is configured by a hole which is opened in the periphery of the display unit 101a, and the physical amount sensor 10 is installed in the inside thereof. In the mobile terminal 100, the physical amount sensor 10 is configured to detect pressure of breath which is blown in the breath-blowing hole 104, or a physical amount other than the pressure if breath is blown in the breath-blowing hole 104. This will be described later.

To begin with, the physical amount sensor 10 will be described.

As illustrated in FIG. 2, the physical amount sensor 10 includes a substrate 2, a deflection amount sensor (pressure detection unit) 3 which is used as a pressure sensor, a temperature sensor (physical amount detection unit) 6, an element surrounding structural body 4, a cavity section 7, and a semiconductor circuit 9.

Substrate

The substrate 2 has a plate shape, and is configured by sequentially laminating a first insulating film 22 which is configured by a silicon oxide film (SiO₂ film), and a second insulating film 23 which is configured by a silicon nitride film (SiN film) on a semiconductor substrate 21 which is configured by an SOI substrate (substrate in which a first Si layer 211, an SiO₂ layer 212, a second Si layer 213 are sequentially laminated). However, a member which is used as the semiconductor substrate 21 is not limited to the SOI substrate, and for example, a silicon substrate can be used. In addition, as a material of the first insulating film 22 and the second insulating film 23, a material which can protect the semiconductor substrate 21 at the time of fabricating, and can insulate between semiconductor substrate 21, the deflection amount sensor 3, and the temperature sensor 6 can be used without a particular limit. In addition, a planar view shape of the substrate 2 is not particularly limited, and can be, for example, a rectangular shape such as a substantially square shape or a substantially oblong shape, or a circular shape, but is a substantially square shape, in the present embodiment.

In addition, a diaphragm 24 which is thinner than a peripheral portion and is deflected by a received pressure is provided on the substrate 2. The diaphragm 24 is formed by providing a concave section 25 having a bottom on a lower surface (second Si layer 213) of the substrate 2, and a lower surface thereof (bottom surface of the concave section 25) is a pressure receiving surface 24a. A planar view shape of the diaphragm 24 is not particularly limited, and can be, for example, a rectangular shape such as a substantially square shape or a substantially oblong shape, or a circular shape, but is a substantially square shape, in the present embodiment. In addition, a width of the diaphragm 24 is not particularly limited, but can be set to be equal to or wider than approximately 400 µm and to be equal to or less than 600 µm. In addition, a thickness of the diaphragm 24 is not particularly limited, but it is preferable that the thickness is equal to or thicker than approximately 10 µm and is equal to or less than 50 µm, for example, and it is more preferable that the thickness is equal to or thicker than 15 µm and is equal to or less than 25 µm. By doing this, the diaphragm 24 can be sufficiently softened, and can be sufficiently deflected.

In addition, the semiconductor circuit (circuit) 9 is formed on the semiconductor substrate 21 and an upper side thereof. In the semiconductor circuit 9, circuit elements, such as an active element such as a MOS transistor, a capacitor, an inductor, a resistor, a diode, and a wire are included. In this way, by forming the semiconductor circuit 9 on the substrate 2, the physical amount sensor 10 can be miniaturized, compared to a case in which the semiconductor circuit 9 is separately provided.

Deflection Amount Sensor

As illustrated in FIG. 2 and FIG. 3, the deflection amount sensor 3 includes four piezoresistor elements (deflection amount detection elements) 31, 32, 33, and 34 which are disposed on the diaphragm 24. Among these, the piezoresistor elements 31 and 32 are disposed so as to correspond to a pair of sides 241 and 242, which face each other, of the diaphragm 24 which is a rectangular shape in a planar view, and the piezoresistor elements 33 and 34 are disposed so as to correspond to a pair of sides 243 and 244, which face each other, of the diaphragm 24 which is a rectangular shape in a planar view.

The piezoresistor element 31 includes a piezoresistor unit 311 which is disposed in an outer edge (periphery of the side 241) of the diaphragm 24. The piezoresistor unit 311 has a longitudinal shape which extends along a direction that is in parallel with the side 241. In addition, wires 313 are respectively coupled to both end portions of the piezoresistor unit 311.

In the same manner, the piezoresistor element 32 includes a piezoresistor unit 321 which is disposed in an outer edge (periphery of the side 242) of the diaphragm 24. The piezoresistor unit 321 has a longitudinal shape which extends along a direction that is in parallel with the side 242. In addition, wires 323 are respectively coupled to both end portions of the piezoresistor unit 321.

Meanwhile, the piezoresistor element 33 includes a pair of piezoresistor units 331 which are disposed in an outer edge (periphery of the side 243) of the diaphragm 24, and a coupling section 332 which is coupled to a pair of piezoresistor units 331. A pair of piezoresistor units 331 are in parallel with each other, and have a longitudinal shape which extends along a direction (the same direction as that of the piezoresistor units 311 and 321) that is perpendicular to the side 243. One end portions of a pair of the piezoresistor units 331 are coupled to each other through a coupling section 332, and wires 333 are respectively coupled to the other end portions of a pair of the piezoresistor units 331.

In the same manner, the piezoresistor element 34 includes a pair of piezoresistor units 341 which are disposed in an outer edge (periphery of the side 244) of the diaphragm 24, and a coupling section 342 which is coupled to a pair of piezoresistor units 341. A pair of piezoresistor units 341 are in parallel with each other, and have a longitudinal shape which extends along a direction (the same direction as that of the piezoresistor units 311 and 321) that is perpendicular to the side 244. One end portions of a pair of the piezoresistor units 341 are coupled to each other through a coupling section 342, and wires 343 are respectively coupled to the other end portions of a pair of the piezoresistor units 341.

As described above, the piezoresistor units 311, 321, 331, and 341 are respectively configured by doping (diffusing or injecting) impurities, such as phosphorus or boron into the first Si layer 211 of the semiconductor substrate 21, for example. In addition, the wires 313, 323, 333, and 343, and the coupling sections 332 and 342 are respectively configured by doping (diffusing or injecting) impurities, such as phosphorus or boron into the first Si layer 211 so as to have higher concentrations than the piezoresistor units 311, 321, 331, and 341 for example.

However, for example, in addition to this, the piezoresistor units 311, 321, 331, and 341 may be configured by forming a polycrystalline silicon film on the diaphragm 24 using a sputtering method, a CVD method, or the like, by patterning the polycrystalline silicon film using etching, and by doping (diffusing or injecting) impurities such as phosphorous or boron into the patterned polycrystalline silicon film. The wires 313, 323, 333, and 343, and the coupling sections 332 and 342 may be configured in the same manner as described above.

In addition, the piezoresistor elements 31, 32, 33, and 34 are configured in such a manner that resistance values in a natural state are equal to each other. Then, the piezoresistor elements 31, 32, 33, and 34 are electrically coupled to each other through the wires 313, 323, 333, and 343, and as illustrated in FIG. 4, configure a bridge circuit 30 (wheatstone bridge circuit). A drive circuit (not illustrated) which supplies a drive voltage AVDC is coupled to the bridge circuit 30. Then, the bridge circuit 30 outputs signals (voltages) according to resistance values of the piezoresistor elements 31, 32, 33, and 34.

Even if an extremely thin diaphragm 24 is used, the deflection amount sensor 3 does not have a problem that Q value is decreased by vibration leakage which flows into the diaphragm 24, in the same manner as in a case in which a vibration element such as a resonator is used as a sensor element. In addition, for example, the piezoresistor elements 31, 32, 33, and 34 are configured by doping impurities such as phosphorous or boron into the first Si layer 211, and thereby the physical amount sensor 10 can have a low profile (thin), compared to a case in which the piezoresistor elements 31, 32, 33, and 34 are provided on an upper surface of the diaphragm 24 so as to overlap each other.

Temperature Sensor

As illustrated in FIG. 3, the temperature sensor 6 includes a piezoresistor element (temperature sensing element) 61 which is provided on the diaphragm 24. The piezoresistor element 61 includes a piezoresistor unit 611 which is disposed in a center section S1 of the diaphragm 24. That is, the piezoresistor unit 611 is positioned on a center side (center O side) of the diaphragm 24 more than the deflection amount sensor 3 (piezoresistor units 311, 321, 331, and 341). In addition, the piezoresistor unit 611 is disposed in parallel with the piezoresistor unit 311, and has a longitudinal shape which extends along a side 241 so as to be in parallel with the piezoresistor unit 311. In addition, wires 613 are respectively coupled to both end portions of the piezoresistor unit 611.

Since the piezoresistor element 61 has a property in which a resistance value is changed by temperature, it is possible to sense temperature of a periphery portion (inside of the deflection amount sensor 3 or the breath-blowing hole 104 which are positioned in the vicinity), based on a resistance value change of the piezoresistor element 61. Particularly, the piezoresistor element 61 is provided in the diaphragm 24, and thereby it is possible to dispose the temperature sensor 6 in a position closer to the deflection amount sensor 3, and to dispose inside the cavity section 7 in the same manner as the deflection amount sensor 3. That is, it is possible to position the temperature sensor 6 in closer circumstances to the deflection amount sensor 3, and to sense more accurately temperature of the deflection amount sensor 3.

For example, the piezoresistor unit 611 is configured by doping (diffusing or injecting) impurities, such as phosphorous or boron, into the first Si layer 211. In addition, for example, the wire 613 is configured by doping (diffusing or injecting) impurities, such as phosphorous, or boron into the first Si layer 211 so as to have higher concentrations than those of the piezoresistor unit 611. The piezoresistor element 61 is configured by doping impurities such as phosphorous or boron into the first Si layer 211, and thereby the temperature sensor 6 can be simply provided, and the physical amount sensor 10 can have a low profile (thin), compared to a case in which other members such as a thermocouple are provided on an upper surface of the diaphragm 24 so as to overlap each other, for example.

However, for example, in addition to this, the piezoresistor units 611, 621, 631, and 641 may be configured by forming a polycrystalline silicon film on the diaphragm 24 using a sputtering method, a CVD method, or the like, by patterning the polycrystalline silicon film using etching, and by doping (diffusing or injecting) impurities such as phosphorous or boron into the patterned polycrystalline silicon film. The wires 313, 323, 333, and 343, and the coupling sections 332 and 342 may be configured in the same manner as described above.

Element Surrounding Structural Body 4

As illustrated in FIG. 2, the element surrounding structural body 4 is formed so as to define the cavity section 7. The element surrounding structural body 4 includes a wall section 51 of a ring shape which is formed so as to surround the deflection amount sensor 3 and the temperature sensor 6, and a cover section 52 which blocks an opening of the cavity section 7 that is surrounded by an inner wall of the wall section 51, on the substrate 2.

The element surrounding structural body 4 includes an interlayer insulating film 41, a wiring layer 42 which is formed on the interlayer insulating film 41, an interlayer insulating film 43 which is formed on the wiring layer 42 and the interlayer insulating film 41, a wiring layer 44 which is formed on the interlayer insulating film 43, a surface protection film 45 which is formed on the wiring layer 44 and the interlayer insulating film 43, and a sealing layer 46. The wiring layer 44 includes a cover layer 441 which includes a plurality of pores 442 which links the inside and the outside of the cavity section 7, and the sealing layer 46 which is disposed on the cover layer 441 seals the pore 442. In the element surrounding structural body 4, the above-described wall section 51 is configured by the interlayer insulating film 41, the wiring layer 42, the interlayer insulating film 43, the wiring layer 44 (however, a portion except the cover layer 441), and the surface protection film 45, and the above-described cover section 52 is configured by the cover layer 441 and the sealing layer 46.

The wiring layers 42 and 44 includes wiring layers 42a and 44a which are formed so as to surround the cavity section 7, and wiring layers 42b and 44b which configure wires of the semiconductor circuit 9. Thus, the semiconductor circuit 9 is drawn on an upper surface of the physical amount sensor 10 by the wiring layers 42b and 44b. In addition, a film. 49 which is formed of, for example, a polycrystalline silicon film is provided between the wiring layer 42a and the second insulating film 23.

The interlayer insulating films 41 and 43 are not particularly limited, but can use an insulating film such as a silicon oxide film ($SiO_2$ film). In addition, the wiring layers 42 and 44 are not particularly limited, but can use a metal film such as an aluminum film. In addition, the sealing layer 46 is not particularly limited, but can use a metal film, such as Al, Cu, W, Ti, or TiN. In addition, the surface protection film 45 is not particularly limited, but can use a material, which has a resistance for protecting an element from moisture, garbage, scratch, or the like, such as a silicon oxide film, a silicon nitride film, a polyimide film, or an epoxy resin film.

Cavity Section

As illustrated in FIG. 2, the cavity section 7 which is defined by the substrate 2 and the element surrounding structural body 4 is a space which is sealed, and functions as a pressure reference chamber which provides a reference value of pressure which is detected by the physical amount sensor 10. The cavity section 7 is disposed so as to overlap the diaphragm 24, and configures a portion of a wall section in which the diaphragm 24 defines the cavity section 7. A state of the inside of the cavity section 7 is not particularly limited, but is preferred to be a vacuum state (for example, equal to or less than 10 Pa). By doing this, the physical amount sensor 10 can be used as an "absolute pressure sensor" which detects pressure using a vacuum state as a reference. For this reason, usability of the physical amount sensor 10 is increased. However, a state of the inside of the cavity section 7 may not be a vacuum state, may be, for example, an atmosphere state, may be a decreased pressure state which is lower in pressure than atmosphere, and may be an increased pressure state which is higher in pressure than atmosphere. In addition, inert gas such as nitride gas or rare gas may fill inside the cavity section 7.

As described above, a configuration of the physical amount sensor 10 is simply described.

In the physical amount sensor 10, the diaphragm 24 is disposed so as to face the breath-blowing hole 104, and when breath is blown into the breath-blowing hole 104, the pressure receiving surface 24a of the diaphragm. 24 responds to pressure of the breath, and thereby the diaphragm 24 is deflected and deformed. As a result, the piezoresistor elements 31, 32, 33, and 34 are distorted, and according to the deflected amount, resistance values of the piezoresistor elements 31, 32, 33, and 34 are changed. In accordance with this, an output of the bridge circuit 30 is changed. Then, as illustrated above, the piezoresistor elements 31, 32, 33, and 34 have a property (temperature dependency of resistance value) in which a resistance value is changed also by temperature (ambient temperature) thereof in addition to deflection thereof. For this reason, a change of the output of the bridge circuit 30 is caused by the deflection of the piezoresistor elements 31, 32, 33, and 34, and the temperature of the piezoresistor elements 31, 32, 33, and 34. From this output (signal), a magnitude of the pressure (absolute pressure) received by the pressure receiving surface 24a cannot be accurately obtained. Thus, in the physical amount sensor 10, temperature of the deflection amount sensor 3 is sensed by the temperature sensor 6, and based on the sensed temperature, a signal which is obtained from the bridge circuit 30 is corrected (an amount of change caused by temperature of the piezoresistor elements 31, 32, 33, and 34 is removed), and based on the corrected signal, a magnitude of the pressure (absolute pressure) which is received by the pressure receiving surface 24a is obtained. By doing this, pressure which is received by the pressure receiving surface 24a can be accurately obtained.

In addition, the temperature sensor 6 performs both a function of a sensor for correcting temperature of the deflection amount sensor 3 described above, and a function in which temperature in the breath-blowing hole 104 that will be describe hereinafter is detected.

In the physical amount sensor 10 described above, each of the deflection amount sensor 3 and the temperature sensor 6 is electrically coupled to the control unit 8.

As illustrated in FIG. 5, the control unit 8 is configured to include a central processing unit (CPU), and includes a determination unit 82 which includes a comparison unit 81. The control unit 8 performs a control of a display unit 101a and the like, or various processing.

The storage unit 11 includes, for example, an electrically erasable programmable read-only memory (EEPROM) which is a kind of a non-volatile semiconductor memory, or the like, and can store a determination reference with which it is determined whether breath is blown or not, various programs, or the like.

In the mobile terminal 100, by spraying breath into the breath-blowing hole 104, an operation of the mobile terminal 100 can be performed, instead of an operation which is performed by the operation buttons 105. As such an operation, there are, for example, ON/OFF operations of a backlight, START/STOP operations of a stopwatch, or the like. According to such configurations, in a case in which both hands have objects, or even in a case in which either of the operation buttons 105 cannot be operated, or it is difficult to operate the operation buttons, because of running or the like, it is possible to operate the mobile terminal 100 by a simple operation such as breath being blown to the breath-blowing hole 104.

In addition, the mobile terminal 100 has a valid configuration in which the mobile terminal 100 is prevented from being unintentionally operated by influence of wind or the like, even in a case in which the mobile terminal 100 is used in the outside or the like. Hereinafter, this will be described. Hereinafter, a case in which ON/OFF of a backlight is operated as an example will be described.

The storage unit 11 stores a determination reference which is a reference of determining whether or not breath is blown into the breath-blowing hole 104. The determination reference includes information (determination reference $P_0$) of a maximum value $P_1$ and a minimum value $P_2$ of pressure, and information (determination reference $T_0$) of maximum value $T_1$ and minimum value $T_2$ of temperature.

The comparison unit 81 compares a signal (hereinafter, referred to as "pressure P") which is detected by the deflection amount sensor 3 and is output, to a determination reference which is stored in the storage unit 11, and also compares a signal (hereinafter, referred to as "temperature T") which is detected by the temperature sensor 6 and is output, to a determination reference which is stored in the storage unit 11.

The determination unit 82 determines whether or not breath is blown, based on a comparison result of the comparison unit 81. In a case in which the comparison result satisfies both ($P_2 \le P \le P_1$) and ($T_2 \le T \le T_1$), the determination unit 82 determines that the breath is blown. In a case in which the determination unit 82 determines that the breath is blown, the control unit 8 turns on a backlight of the display unit 101a.

Meanwhile, in a case in which the comparison result does not satisfy both ($P_2 \le P \le P_1$) and ($T_2 \le T \le T_1$), that is, the comparison result is any one of ($P > P_1$, $P < P_2$, $T > T_1$, and $T < T_2$), the determination unit 82 determines that the breath is not blown. In this case, the control unit 8 does not turn on the backlight.

In this way, the mobile terminal 100 can operate ON/OFF of the backlight, only in a case in which the comparison result of the comparison unit 81 satisfies both ($P_2 \le P \le P_1$) and ($T_2 \le T \le T_1$). For this reason, for example, even in a case in which a comparison result is ($P_2 \le P \le P_1$) due to an influence of wind, as long as ($T_2 \le T \le T_1$) is not satisfied, an operation of ON/OFF of the backlight is not performed.

In this way, according to the invention, the pressure P and the temperature T of the breath-blowing hole 104 are respectively detected, and detection results of the pressure and the temperature are compared to the determination reference. By doing this, compared to a case in which only pressure P is detected and is compared to the determination reference, it is possible to prevent or suppress an unintentional operation of ON/OFF of a backlight due to an affection of wind. Thus, it is possible to accurately detect whether or not breath is blown. As a result, it is possible to reduce power consumption caused by an unintentional operation of the mobile terminal 100, and to prevent or suppress unnecessary consumption of a battery.

A user sprays breath into the breath-blowing hole 104 in advance, pressure P and temperature T in the breath-blowing hole 104 at that time are measured, and based on a measurement result, a maximum value $P_1$ and a minimum value $P_2$ of pressure, and a maximum value $T_1$ and a minimum value $T_2$ of temperature can be respectively set. By doing this, a difference in pressure P and temperature T of breath for each user can be reflected to the determination reference. Thus, it is possible to detect more accurately whether or not breath is blown.

In addition, as described above, in the physical amount sensor 10, since the deflection amount sensor 3 and the temperature sensor 6 are integrally configured, the deflection amount sensor 3 and the temperature sensor 6 can be configured as one element. By doing this, a pressure sensor and a temperature sensor can be configured as one element. Thus, it is possible to simplify a configuration of the breath detection device 1 and to miniaturize the breath detection device, by integrally configuring the deflection amount sensor 3 and the temperature sensor 6, compared to a case in which the pressure sensor and the temperature sensor are separately provided. Furthermore, the deflection amount sensor 3 and the temperature sensor 6 can be closely disposed, and temperature T of the breath-blowing hole 104 can be detected as accurately as possible.

In addition, as illustrated above, the temperature sensor 6 performs both a function of a sensor for correcting temperature of the deflection amount sensor 3, and a function in which temperature in the breath-blowing hole 104 is detected. By doing this, the deflection amount sensor 3 can more accurately detect the pressure P, and can omit a separate provision of a sensor for correcting temperature of the deflection amount sensor 3, and a sensor which detects temperature in the breath-blowing hole 104. Thus, the physical amount sensor 10 can accurately detect the pressure P and can be remarkably miniaturized.

In addition, differently from the above description, the maximum value $P_1$ of pressure and the minimum value $P_2$ of pressure, and the maximum value $T_1$ of temperature and the minimum value $T_2$ of temperature may be set to a predetermined value in advance.

Next, an operation of the mobile terminal 100 will be described using the flowchart of FIG. 6.

To begin with, breath is blown into the breath-blowing hole 104. At this time, pressure P and temperature T are detected by signals from the deflection amount sensor 3 and the temperature sensor 6 (step S101).

Next, based on the detection result in step S101, the comparison unit 81 compares the pressure P with the determination reference $P_0$ and compares the temperature T with the determination reference $T_0$ (step S102).

Then, based on the comparison result which is obtained by comparison of the comparison unit 81, the determination unit 82 determines whether or not both $(P_2 \leq P \leq P_1)$ and $(T_2 \leq T \leq T_1)$ are satisfied (step S103).

In step S103, in a case in which both $(P_2 \leq P \leq P_1)$ and $(T_2 \leq T \leq T_1)$ are satisfied, a backlight of the display unit 101a is turned on (step S104).

Then, in a case in which the backlight that is in a lighting state is turned off, breath is blown into the breath-blowing hole 104 again. At this time, the pressure P and the temperature T are detected by the signals from the deflection amount sensor 3 and the temperature sensor 6 (step S105).

Next, based on the detection result in step S105, the comparison unit 81 compares the pressure P with the determination reference and compares the temperature T with the determination reference (step S106).

Then, based on the comparison result which is obtained by comparison of the comparison unit 81, the determination unit 82 determines whether or not both $(P_2 \leq P \leq P_1)$ and $(T_2 \leq T \leq T_1)$ are satisfied (step S107).

In step S103, in a case in which both $(P_2 \leq P \leq P_1)$ and $(T_2 \leq T \leq T_1)$ are satisfied, a backlight of the display unit 101a is turned off (step S108).

In step S103, in a case in which the comparison result does not satisfy both $(P_2 \leq P \leq P_1)$ and $(T_2 \leq T \leq T_1)$, that is, it is determined that the comparison result is anyone of $(P > P_1, P < P_2, T > T_1,$ and $T < T_2)$, the processing returns to step S101. In this case, the backlight does not turn on. In the same manner, in step S107, in a case in which it is determined that both $(P_2 \leq P \leq P_1)$ and $(T_2 \leq T \leq T_1)$ are not satisfied, the processing returns to step S105. In this case, the backlight does not turn off.

Second Embodiment

Next, a second embodiment of the breath detection device according to the invention will be described.

Figure 7:
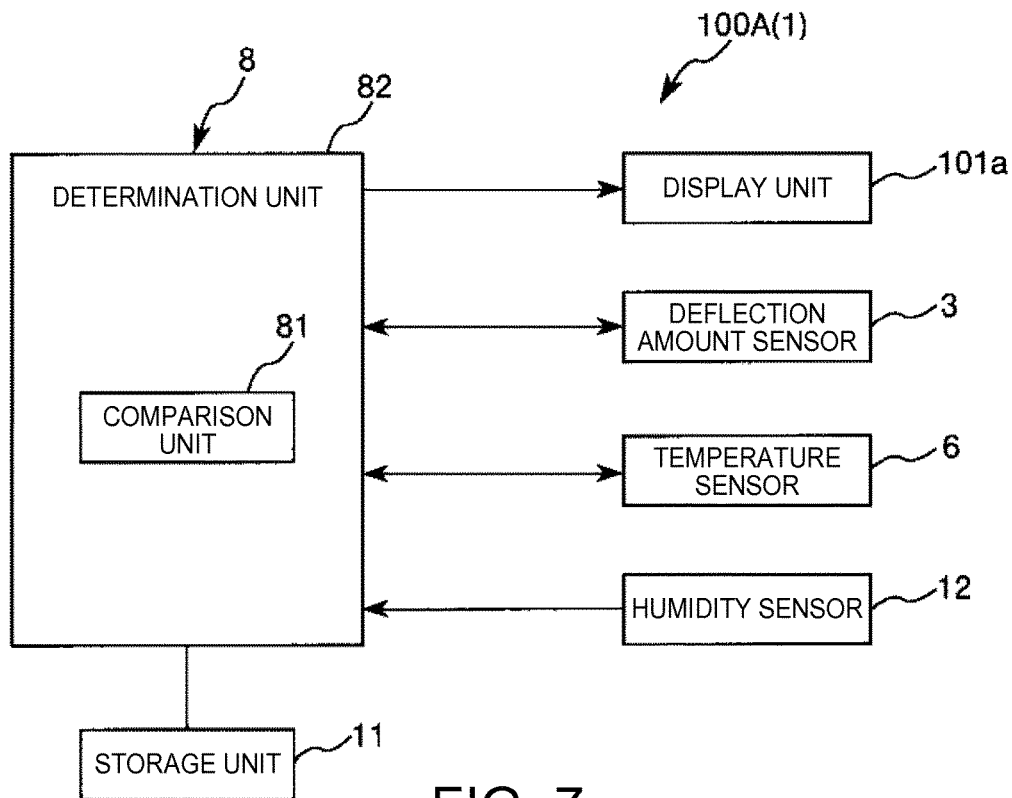
FIG. 7 is a block diagram illustrating a configuration according to a second embodiment of the breath detection device according to the invention.

FIG. 7 is a block diagram illustrating a configuration according to the second embodiment of the breath detection device according to the invention.

Hereinafter, the second embodiment of the breath detection device according to the invention will be described with reference to the figure, but different points from the embodiment described above will be mainly described, and description of the same points will be omitted.

The second embodiment is substantially the same as the first embodiment except that a humidity sensor is provided.

As illustrated in FIG. 7, a mobile terminal 100A includes a humidity sensor (physical amount detection unit) 12 which detects humidity. The humidity sensor 12 is disposed inside the breath-blowing hole 104. For this reason, the humidity sensor 12 can detect humidity in the breath-blowing hole 104.

In addition, the humidity sensor 12 is electrically coupled to the control unit 8, and a signal (hereinafter, referred to as "humidity H") which is detected by the humidity sensor 12 and is output is input to the control unit 8.

In addition, a determination reference which is stored in the storage unit 11 includes information of a maximum value $H_1$ and a minimum value $H_2$ of the humidity H.

The comparison unit 81 compares the pressure P which is detected by the deflection amount sensor 3 with the determination reference, compares the temperature T which is detected by the temperature sensor 6 with the determination reference, and furthermore, compares humidity H which is detected by the humidity sensor 12 with the determination reference.

Based on the comparison result which is obtained by comparison of the comparison unit 81, the determination unit 82 determines whether or not breath is blown. In a case in which the comparison result satisfies all of $(P_2 \leq P \leq P_1)$, $(T_2 \leq T \leq T_1)$, and $(H_2 \leq H \leq H_1)$, the determination unit 82 determines that the breath is blown. In a case in which the determination unit 82 determines that the breath is blown, the control unit 8 turns on a backlight of the display unit 101a.

Meanwhile, in a case in which the comparison result does not satisfy any one of $(P_2 \leq P \leq P_1)$, $(T_2 \leq T \leq T_1)$, and $(H_2 \leq H \leq H_1)$, the determination unit 82 determines that breath is not blown. In this case, the control unit 8 does not turn on the backlight.

In this way, according to the present embodiment, when detecting whether or not breath is blown, the humidity H can also be a reference of determination, in addition to the pressure P and the temperature T. For this reason, the humidity H also becomes a reference of determination, and it is possible to more accurately detect whether or not breath is blown.

Third Embodiment

Next, a third embodiment of the breath detection device according to the invention will be described.

Figure 8:
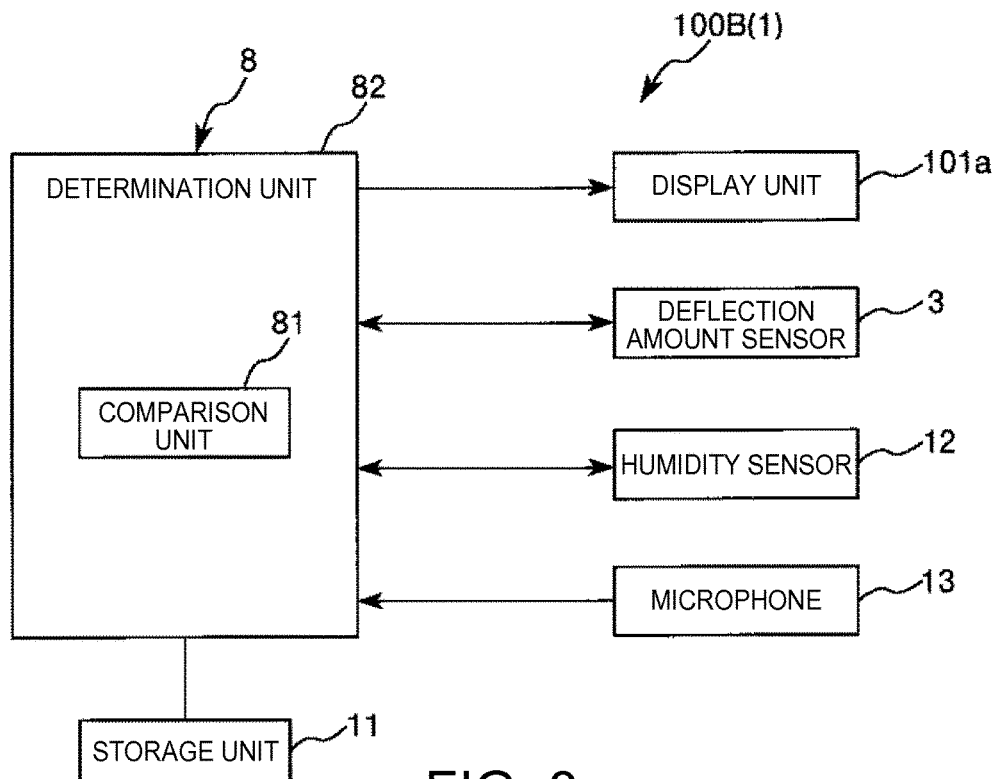
FIG. 8 is a block diagram illustrating a configuration according to a third embodiment of the breath detection device according to the invention.

FIG. 8 is a block diagram illustrating the third embodiment of the breath detection device according to the invention.

Hereinafter, the third embodiment of the breath detection device according to the invention will be described with reference to the figure, but different points from the embodiments described above will be mainly described, and description of the same points will be omitted.

The third embodiment is substantially the same as the second embodiment except that a microphone is provided instead of the humidity sensor.

As illustrated in FIG. 8, in a mobile terminal 100B, a microphone (physical amount detection unit) 13 which detects an audio is provided, instead of the humidity sensor 12 in the second embodiment. The microphone 13 is electrically coupled to the control unit 8, and a signal (hereinafter, referred to as "frequency F") which is detected by the microphone 13 and is output is input to the control unit 8.

In addition, a determination reference which is stored in the storage unit 11 includes reference data which becomes a reference. The reference data is audio data which is recorded in advance in the breath detection device 1 by a user, and includes a maximum value $F_1$ and a minimum value $F_2$ of the frequency.

The comparison unit 81 compares the pressure P which is detected by the deflection amount sensor 3 with the determination reference, compares the temperature T which is detected by the temperature sensor 6 with the determination reference, and furthermore, compares the frequency F of an audio which is detected by the microphone 13 with the determination data.

In a case in which the comparison result satisfies all of ($P_2 \leq P \leq P_1$), ($T_2 \leq T \leq T_1$), and ($F_2 \leq F \leq F_1$), the determination unit 82 determines that the breath is blown. In a case in which the determination unit 82 determines that the breath is blown, the control unit 8 turns on a backlight of the display unit 101a.

Meanwhile, in a case in which the comparison result does not satisfy any one of ($P_2 \leq P \leq P_1$), ($T_2 \leq T \leq T_1$), and ($F_2 \leq F \leq F_1$), the determination unit 82 determines that breath is not blown. In this case, the control unit 8 does not turn on the backlight.

In this way, according to the present embodiment, when detecting whether or not breath is blown, the frequency F of an audio also becomes a reference of determination, in addition to the pressure P and the temperature T. For this reason, the frequency F also becomes a reference of determination, and so far forth, it is possible to more accurately detect whether or not breath is blown.

Figure 9:
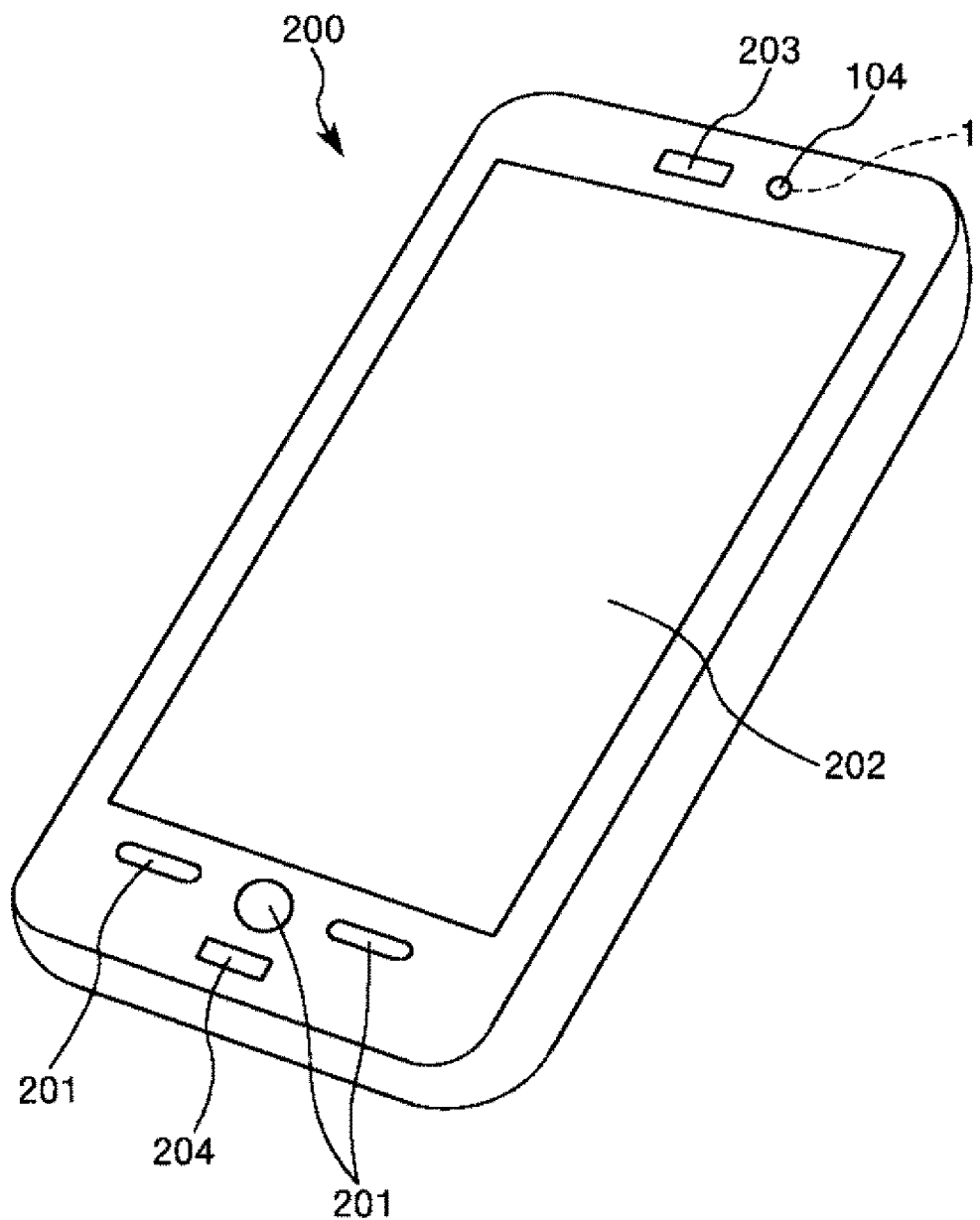
FIG. 9 is a perspective diagram illustrating another form of a mobile terminal that includes a breath detection device according to the invention.

Next, another form of the mobile terminal to which the breath detection device according to the invention is applied will be described. FIG. 9 is a perspective diagram illustrating another form of the mobile terminal that includes the breath detection device according to the invention.

A mobile terminal 200 which is illustrated in FIG. 9 is a device of a smart phone type which includes a plurality of operation buttons 201, a touch panel 202, a voice receiving hole 203, a voice transmitting hole 204, a breath-blowing hole 104, and a breath detection device 1.

The breath-blowing hole 104 is provided in the vicinity of the voice receiving hole 203, and the breath detection device 1 is disposed inside the breath-blowing hole 104.

The mobile terminal 200 is gripped by one hand, and the operation buttons 201 and the touch panel 202 are operated by the other hand. However, in the mobile terminal 200, even in a situation in which the other hand is not used, breath is blown into the breath-blowing hole 104, and thereby operation thereof can be performed.

The mobile terminal of the embodiment of the invention also includes a feature phone (so-called Galapagos mobile phone), a PHS, or the like, in addition to the above-described smart phone.

As described above, embodiments which illustrate the breath detection device, the mobile terminal, and the time display device according to the invention are described, but the invention is not limited to these. Each unit which configures the breath detection device, the mobile terminal, and the time display device of the embodiment of the invention can be replaced with an arbitrary configuration which can perform the same functions. In addition, an arbitrary configuration object may be added.

In addition, the breath detection device, the mobile terminal, and the time display device of the embodiment of the invention may be a combination of two or more arbitrary configurations (characteristics), among the respective embodiments.

A breath detection unit is described as a breath-blowing hole, but in the invention, the breath detection unit also includes an internal surface of a breath-blowing hole, a pressure receiving surface of a diaphragm, or the like.

In addition, the second embodiment describes a case in which, if the comparison result satisfies all of ($P_2 \leq P \leq P_1$) ($T_2 \leq T \leq T_1$), and ($H_2 \leq H \leq H_1$), the determination unit determines that the breath is blown, but the invention is not limited to this. The invention may be configured for the determination unit to determine that the breath is blown in a case in which the comparison result satisfies two of ($P_2 \leq P \leq P_1$), ($T_2 \leq T \leq T_1$), and ($H_2 \leq H \leq H_1$). With regard to this, the third embodiment is also the same as the second embodiment.

In addition, a way in which breath is blown is changed, and thereby a function of an operation may differ. In accordance with, for example, rhythm (number of times, length, strength) in which breath is blown, or the like, the invention can be configured so as to perform an operation of a backlight, an operation of a stopwatch, or the like. In this case, determination references for each function are stored in a storage unit.

In addition, the third embodiment compares audio data which is detected by a microphone with a frequency of a reference data, but the invention is not limited to this. The invention may perform a comparison using two or more of frequency, waveform data, and sound pressure.

In addition, in the respective embodiments, a case in which a physical amount detection unit includes a temperature sensor, a humidity sensor, and a microphone, is described, but the invention is not limited to this. For example, the invention may include an optical sensor, a gas concentration sensor, an odor sensor, or the like.

What is claimed is:

1. A breath detection device comprising:
a breath-blowing inlet in which breath is blown;
a pressure detector that detects pressure which is received by the breath-blowing inlet, and outputs a first signal;
a physical amount detector that detects a temperature and outputs a second signal, the physical amount detector including a temperature sensor that detects the temperature, wherein the first signal output by the pressure detector is corrected utilizing information relating to the temperature detected by the temperature sensor;
a storage portion that stores a determination reference; and a determination portion determines whether breath is blown in the breath-blowing inlet, wherein the determination reference includes (i) a first determination reference including an upper limit value and a lower limit value of the pressure and (ii) a second determination reference including an upper limit value and a lower limit value of the temperature, wherein the determination portion compares the pressure detected from the first signal with the first determination reference, compares the temperature detected from the second signal with the second determination reference, and determines that breath is blown in the breath-blowing inlet if both the detected pressure and the detected temperature are values between the upper limit value and the lower limit value of the corresponding determination reference, and wherein when the determination portion determines that breath is blown in the breath-blowing inlet, operation of a backlight or a stopwatch is performed.

2. The breath detection device according to claim 1, wherein the pressure detector includes a pressure sensor, and wherein the pressure sensor and the temperature sensor are integrally configured.

3. The breath detection device according to claim 1, further comprising a humidity sensor.

4. The breath detection device according to claim 1, further comprising a microphone.

5. The breath detection device according to claim 4, wherein the determination reference includes reference data that is a reference, and wherein data of an audio that is detected by the microphone is compared with the reference data.

6. The breath detection device according to claim 1, wherein the determination reference is set based on information on breath that is blown in advance into the breath-blowing inlet.

7. A mobile terminal comprising:
the breath detection device according to claim 1.

8. A time display device comprising:
the breath detection device according to claim 1.

9. A breath detection device comprising:
a breath-blowing inlet in which breath is blown;
a pressure detector that detects pressure which is received by the breath-blowing inlet, and outputs a signal;
a physical amount detector that includes a temperature sensor that detects a temperature, and that includes a microphone that detects an audio frequency and outputs a signal based upon the detected temperature and an other signal based upon the detected audio frequency, wherein the signal output by the pressure detector is corrected utilizing information relating to the temperature detected by the temperature sensor;
a storage that stores a determination reference to determine whether or not breath is blown into the breath-blowing inlet; and
a comparator configured to compare the signal output from the pressure detector and the signals output from the physical amount detector with the determination reference, and to determine, based upon the comparison, whether or not breath is blown into the breath-blowing inlet, wherein the determination reference includes reference data that is a reference, wherein data of an audio that is detected by the microphone is compared with the reference data, and wherein when the determination portion determines that breath is blown in the breath-blowing inlet, operation of a backlight or a stopwatch is performed.

10. A mobile terminal comprising:
the breath detection device according to claim 9.

* * * * *